(12) United States Patent
Jablonski et al.

(10) Patent No.: US 11,529,508 B2
(45) Date of Patent: Dec. 20, 2022

(54) WEARABLE ACCESSORY FOR VENTRICULAR ASSIST SYSTEM

(71) Applicant: TC1 LLC, St. Paul, MN (US)

(72) Inventors: Brendan Jablonski, Somerville, MA (US); Alison Lepordo, Tewksbury, MA (US); Kaitlyn Spink, Methuen, MA (US)

(73) Assignee: TC1 LLC, St. Paul, MN (US)

( * ) Notice: Subject to any disclaimer, the term of this patent is extended or adjusted under 35 U.S.C. 154(b) by 0 days.

(21) Appl. No.: 16/290,269

(22) Filed: Mar. 1, 2019

(65) Prior Publication Data

US 2019/0269838 A1    Sep. 5, 2019

Related U.S. Application Data

(60) Provisional application No. 62/637,780, filed on Mar. 2, 2018.

(51) Int. Cl.
*A45C 15/00*    (2006.01)
*A61M 60/148*    (2021.01)
(Continued)

(52) U.S. Cl.
CPC ........... *A61M 60/148* (2021.01); *A45C 11/00* (2013.01); *A45C 13/02* (2013.01); *A45C 13/10* (2013.01);
(Continued)

(58) Field of Classification Search
CPC .............. A61M 1/122; A61M 1/1086; A61M 2205/0216; A61M 2205/8206;
(Continued)

(56) References Cited

U.S. PATENT DOCUMENTS 44,993 A     11/1864  Woods
2,625,192 A   1/1953  Kinskie
(Continued)

FOREIGN PATENT DOCUMENTS

JP    61502030 A    9/1986
JP    05329121 A    12/1993
(Continued)

*Primary Examiner* — Nathan J Newhouse
*Assistant Examiner* — Matthew T. Theis
(74) *Attorney, Agent, or Firm* — Kilpatrick Townsend & Stockton LLP (57) ABSTRACT

The invention relates generally to wearable accessory carriers for mechanical circulatory support systems, and more specifically relates to belts for carrying peripheral components of a VAD. Such wearable accessory carriers may be suitable for carrying and retaining peripheral components of the VAD in a safe, comfortable, and convenient manner. In certain aspects, the invention provides a wearable accessory carrier configured as an elastic belt with several pockets for holding peripheral components. In other aspects, a wearable accessory carrier may be configured as a belt with a magnetic strip configured to carry one or more modular compartments or pockets for holding peripheral components via magnetic attachment. The wearable accessory carriers disclosed herein may be sized to fit around or configured to be worn on a patient's waist, lower or upper torso, thigh, calf, arm, or other limb.

24 Claims, 3 Drawing Sheets

(51) Int. Cl.
*A45C 11/00* (2006.01)
*A45C 13/10* (2006.01)
*A45C 13/02* (2006.01)
*A61M 60/857* (2021.01)
*A61M 60/88* (2021.01)
*A61M 60/178* (2021.01)
*A61M 60/585* (2021.01)
*A61M 60/878* (2021.01)

(52) U.S. Cl.
CPC ........... *A45C 15/00* (2013.01); *A61M 60/178* (2021.01); *A61M 60/585* (2021.01); *A61M 60/857* (2021.01); *A61M 60/878* (2021.01); *A61M 60/88* (2021.01); *A45C 2013/1015* (2013.01); *A61M 2205/0216* (2013.01); *A61M 2205/0288* (2013.01); *A61M 2205/8206* (2013.01); *A61M 2209/088* (2013.01)

(58) Field of Classification Search
CPC .... A61M 2209/088; A61M 2205/0288; A61M 1/1012; A61M 1/127; A61M 60/148; A61M 60/178; A61M 60/585; A61M 60/857; A61M 60/878; A61M 60/88; A45C 11/00; A45C 13/02; A45C 15/00; A45C 2013/1015; A45C 13/10; A45C 13/1069; A45C 1/04
USPC .................................................. 224/183, 660
See application file for complete search history.

(56) References Cited

U.S. PATENT DOCUMENTS

| | | |
|---|---|---|
| 3,919,615 A | 11/1975 | Niecke |
| 4,214,688 A | 7/1980 | Griffin et al. |
| 4,384,372 A | 5/1983 | Rector |
| 4,411,267 A | 10/1983 | Heyman |
| 4,433,803 A * | 2/1984 | Liberboim ........... A63B 47/001 224/251 |
| 4,600,134 A | 7/1986 | Colby et al. |
| 4,793,486 A | 12/1988 | Konopka et al. |
| 5,059,182 A | 10/1991 | Laing et al. |
| 5,152,443 A | 10/1992 | Hagan |
| 5,186,290 A | 2/1993 | Takayama |
| 5,211,321 A | 5/1993 | Rodriguez |
| 5,259,093 A | 11/1993 | D'Annunzio et al. |
| 5,263,618 A | 11/1993 | Talavera et al. |
| 5,284,470 A | 2/1994 | Beltz |
| 5,358,159 A | 10/1994 | Lundie, Jr. |
| 5,392,973 A | 2/1995 | Benson |
| D358,475 S | 5/1995 | Choksi et al. |
| 5,524,802 A | 6/1996 | Benson et al. |
| 5,613,935 A | 3/1997 | Jarvik |
| 5,630,536 A | 5/1997 | Bugnaski |
| 5,653,367 A | 8/1997 | Abramson |
| 5,695,471 A | 12/1997 | Wampler |
| 5,727,720 A | 3/1998 | Thatcher et al. |
| 5,741,306 A | 4/1998 | Glegyak et al. |
| 5,746,365 A | 5/1998 | Scott et al. |
| 5,775,558 A | 7/1998 | Montalbano |
| 5,816,460 A | 10/1998 | Cook |
| 5,888,242 A | 3/1999 | Antaki et al. |
| 5,915,609 A | 6/1999 | Diakoulas |
| 6,015,399 A | 1/2000 | Mracna et al. |
| 6,029,871 A | 2/2000 | Park |
| 6,071,093 A | 6/2000 | Hart |
| 6,116,862 A | 9/2000 | Rau et al. |
| 6,186,665 B1 | 2/2001 | Maher et al. |
| 6,234,772 B1 | 5/2001 | Wampler et al. |
| 6,264,635 B1 | 7/2001 | Wampler et al. |
| 6,289,896 B1 | 9/2001 | Hart et al. |
| 6,325,260 B1 * | 12/2001 | Gorham ................... A45C 1/04 206/69 |
| 6,543,661 B1 | 4/2003 | Lazur et al. |
| 6,561,814 B2 | 5/2003 | Tilbury et al. |
| 6,568,575 B1 | 5/2003 | Bartholomew et al. |
| 6,681,404 B1 | 1/2004 | Adlard et al. |
| 6,688,861 B2 | 2/2004 | Wampler |
| 6,698,631 B1 | 3/2004 | Haskins et al. |
| 6,752,299 B2 | 6/2004 | Moberg et al. |
| 6,923,302 B2 | 8/2005 | Godshaw et al. |
| 6,923,357 B2 | 8/2005 | Smith et al. |
| 6,991,595 B2 | 1/2006 | Burke et al. |
| 7,282,044 B2 | 10/2007 | Sisk et al. |
| 7,370,781 B2 | 5/2008 | Gambrill et al. |
| 7,563,225 B2 * | 7/2009 | Sugiura ............... A61M 60/148 600/17 |
| 7,699,586 B2 | 4/2010 | LaRose et al. |
| 7,770,770 B2 | 8/2010 | Murdoch et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,152,493 B2 | 4/2012 | LaRose et al. |
| 8,302,830 B1 | 11/2012 | Jensen et al. |
| 8,323,174 B2 | 12/2012 | Jeevanandam et al. |
| 8,449,444 B2 | 5/2013 | Poirier |
| 8,506,471 B2 | 8/2013 | Bourque |
| 8,597,350 B2 | 12/2013 | Rudser et al. |
| 8,652,024 B1 | 2/2014 | Yanai et al. |
| 8,657,733 B2 | 2/2014 | Ayre et al. |
| 8,668,473 B2 | 3/2014 | LaRose et al. |
| 8,807,412 B2 | 8/2014 | Thomas et al. |
| 2002/0170933 A1 | 11/2002 | Martin et al. |
| 2004/0129749 A1 | 7/2004 | Hassett |
| 2005/0059935 A1 * | 3/2005 | Yamazaki ............. A61B 50/13 604/179 |
| 2005/0071001 A1 | 3/2005 | Jarvik |
| 2006/0211937 A1 | 9/2006 | Eldridge et al. |
| 2007/0078293 A1 | 4/2007 | Shambaugh, Jr. et al. |
| 2008/0021394 A1 | 1/2008 | LaRose et al. |
| 2008/0027341 A1 | 1/2008 | Sackner et al. |
| 2009/0039120 A1 | 2/2009 | Murdoch et al. |
| 2009/0203957 A1 | 8/2009 | LaRose et al. |
| 2010/0122995 A1 | 5/2010 | Thomas et al. |
| 2012/0046514 A1 | 2/2012 | Bourque |
| 2012/0095281 A1 | 4/2012 | Reichenbach et al. |
| 2013/0048695 A1 * | 2/2013 | Do ............................. A45F 3/14 224/676 |
| 2013/0096364 A1 | 4/2013 | Reichenbach et al. |
| 2013/0121821 A1 | 5/2013 | Ozaki et al. |
| 2013/0170970 A1 | 7/2013 | Ozaki et al. |
| 2013/0225909 A1 | 8/2013 | Dormanen et al. |
| 2013/0314047 A1 | 11/2013 | Eagle et al. |
| 2014/0158734 A1 * | 6/2014 | Bickert ................. F41C 33/048 224/587 |
| 2014/0263499 A1 * | 9/2014 | Carter-Cohen ......... A45F 5/022 224/267 |
| 2016/0296685 A1 * | 10/2016 | Wu ...................... A61M 1/1629 |
| 2018/0049493 A1 * | 2/2018 | Graves ................... A41D 27/20 |

FOREIGN PATENT DOCUMENTS

| | | |
|---|---|---|
| JP | 11262406 A | 9/1999 |
| JP | 2000051373 A | 2/2000 |
| JP | 2000500992 A | 2/2000 |
| JP | 2005342435 A | 12/2005 |
| JP | 2005342436 A | 12/2005 |
| JP | 2006525062 A | 11/2006 |

* cited by examiner

WEARABLE ACCESSORY FOR VENTRICULAR ASSIST SYSTEM

CROSS-REFERENCE TO RELATED APPLICATIONS

The present application claims the benefit of U.S. Provisional Application No. 62/637,780 filed Mar. 2, 2018, the entire contents of which is incorporated by reference herein in its entirety for all purposes.

BACKGROUND

This application relates generally to wearable accessory carriers for mechanical circulatory support systems, and more specifically relates to belts for carrying peripheral components of a ventricular assist device.

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

The VAD is powered and may also be controlled by a driveline cable that extends from the VAD and through an exit site of the patient to an external power source and/or controller unit. The driveline cable may terminate in a connector having a connector adapted to connect to a corresponding connector receptacle of an external power source and/or controller worn by the patient. Because the peripheral components (e.g., power source(s), controller(s), cable(s)) including a portion of the driveline cable may be positioned outside the patient, it would be desirable to provide improved systems and methods for carrying or retaining the peripheral components in a safe and comfortable manner, while also preventing the driveline cable from pulling on the exit site of the patient.

BRIEF SUMMARY

The invention relates generally to wearable accessory carriers for mechanical circulatory support systems, and more specifically relates to belts for carrying peripheral components of a VAD. Such wearable accessory carriers may be suitable for carrying and retaining peripheral components of the VAD in a safe, comfortable, and convenient manner. In certain aspects, the invention provides a wearable accessory carrier configured as an elastic belt with several pockets for holding peripheral components. In other aspects, a wearable accessory carrier may be configured as a belt with a magnetic strip configured to carry one or more modular compartments or pockets for holding peripheral components via magnetic attachment. The wearable accessory carriers disclosed herein may be sized to fit around or configured to be worn on a patient's waist, lower or upper torso, thigh, calf, arm, or other limb.

In one aspect, a wearable accessory carrier for carrying peripheral components of a blood pump system in accordance with embodiments of the present invention includes an elastic belt configured to be worn on a patient with an implanted blood pump system. The belt includes a plurality of integrated compartments disposed around inner and outer circumferences of the belt. The integrated compartments are configured to carry peripheral components of the blood pump system. In some embodiments, the elastic belt is reversible such that either the inner or outer circumference compartments may face outward away from the patient when the belt is worn by the patient. In some embodiments, the belt includes a non-slip material disposed on the inner circumference of the belt.

In certain embodiments, the belt is made of neoprene. In some embodiments, the plurality of integrated compartments have substantially equivalent sizes. In some embodiments, the plurality of integrated compartments are sized such that a blood pump controller may be positioned vertically and horizontally within each compartment. The plurality of integrated compartments can be sized such that a blood pump battery may be positioned vertically and horizontally within each compartment. The belt can include retention mechanisms configured to secure at least a portion of a driveline cable of the blood pump system in position on the belt. The plurality of integrated compartments can be accessible via slit openings in the belt. In some embodiments, the slit openings of the plurality of integrated compartments include flaps configured to cover the openings. The plurality of integrated compartments can include fasteners. The belt can be configured to be worn on a waist of a patient. The belt can be configured to be worn on a limb of a patient. The belt can include a fastener configured to secure the belt on the patient.

In another aspect, a wearable accessory carrier for carrying peripheral components of a blood pump system is provided that includes a belt configured to be worn on a patient with an implanted blood pump system includes a magnetic strip extending lengthwise along the belt. The belt includes at least one storage compartment configured to carry at least one peripheral component of the blood pump system. The storage compartment includes a magnet such that the storage compartment is detachably couplable to multiple positions on the magnetic strip of the belt. In some embodiments, the belt is made of an elastic material. In some embodiments, the at least one storage compartment includes a flap cover configured to be secured over an opening of the storage compartment. In some embodiments, the at least one storage compartment includes a first storage compartment and a second storage compartment and the first storage compartment is configured to carry a blood pump controller and the second storage compartment is configured to carry a blood pump battery.

In further aspects, a wearable accessory carrier for carrying peripheral components of a blood pump system is provided that includes a belt configured to be worn on a patient with an implanted blood pump system and a hook and loop strip extending lengthwise along the belt. The belt includes at least one storage compartment configured to carry at least one peripheral component of the blood pump system. The storage compartment includes a hook and loop fastener such that the storage compartment is detachably couplable to multiple positions on the hook and loop strip of the belt. In some embodiments, the belt is made of an elastic material. In some embodiments, the at least one storage compartment includes a flap cover configured to be secured over an opening of the storage compartment. In some embodiments, the at least one storage compartment includes a first storage compartment and a second storage compartment and the first storage compartment is configured to carry a blood pump controller and the second storage compartment is configured to carry a blood pump battery.

DETAILED DESCRIPTION

Figure 1:
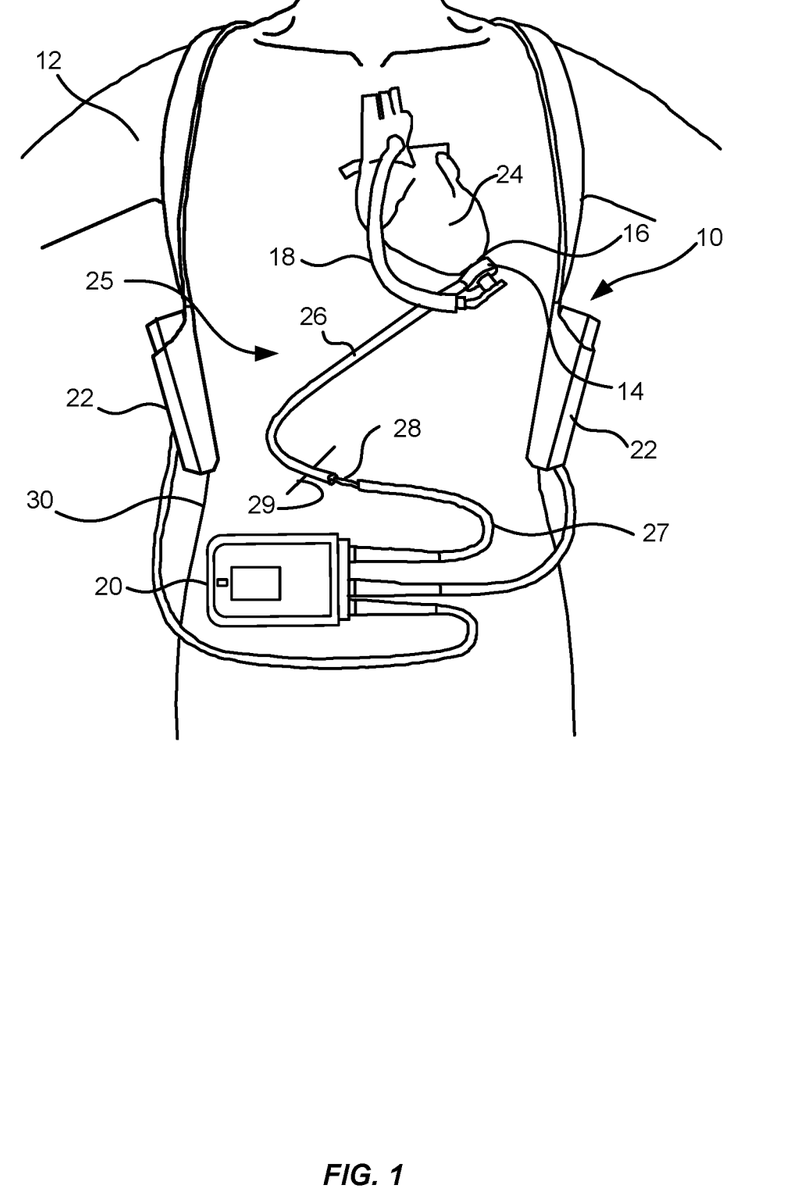
FIG. 1 is an illustration of an implanted mechanical circulatory support system with a driveline cable in accordance with aspects of the invention.

FIG. 1 is an illustration of a mechanical circulatory support system 10 (e.g., a blood pump system) implanted in a patient's body 12. The mechanical circulatory support system 10 comprises an implantable blood pump 14, ventricular cuff 16, outflow cannula 18, system controller 20, and a power supply (e.g., one or more batteries 22). The implantable blood pump 14 may comprise a VAD that is attached to an apex of the left ventricle, as illustrated, or the right ventricle, or two or more VADS attached to both ventricles of the heart 24. The VAD may comprise a centrifugal (as shown) or axial flow pump that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety. The blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1 illustrates the mechanical circulatory support system 10 during battery 22 powered operation. A driveline cable 25 (e.g., a percutaneous cable or lead) connects the implanted blood pump 14 to the system controller 20, which monitors system 10 operation. The driveline cable 25 may include a percutaneous portion 26 that exits the patient through an exit site 29 (e.g., abdominal aperture) and terminates at in-line connector 28 that connects the percutaneous portion 26 with a modular external cable 27, the other end of the modular external cable 27 being protected within the system controller 20.

The system controller 20 monitors system operations. Related controller systems applicable to the present invention are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety. The system may be powered by either one, two, or more batteries 22 or other power sources.

Figure 2:
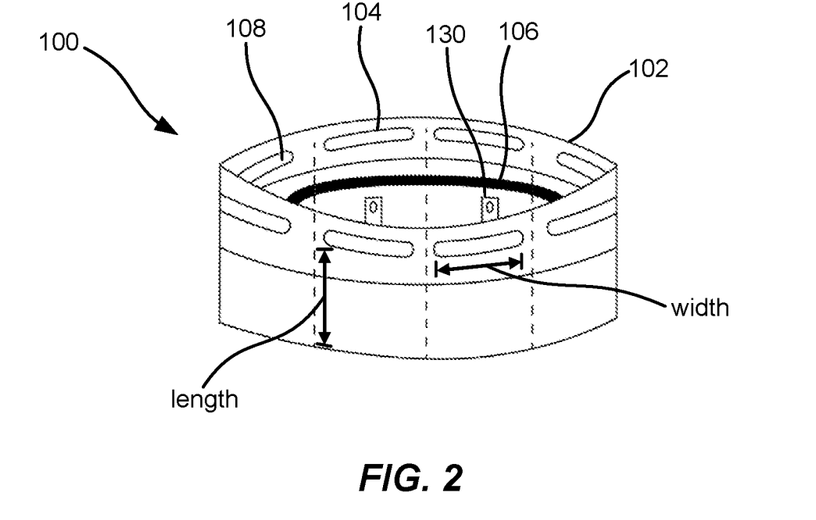
FIG. 2 is an illustration of an exemplary wearable accessory carrier in accordance with aspects of the invention.
Figure 3:
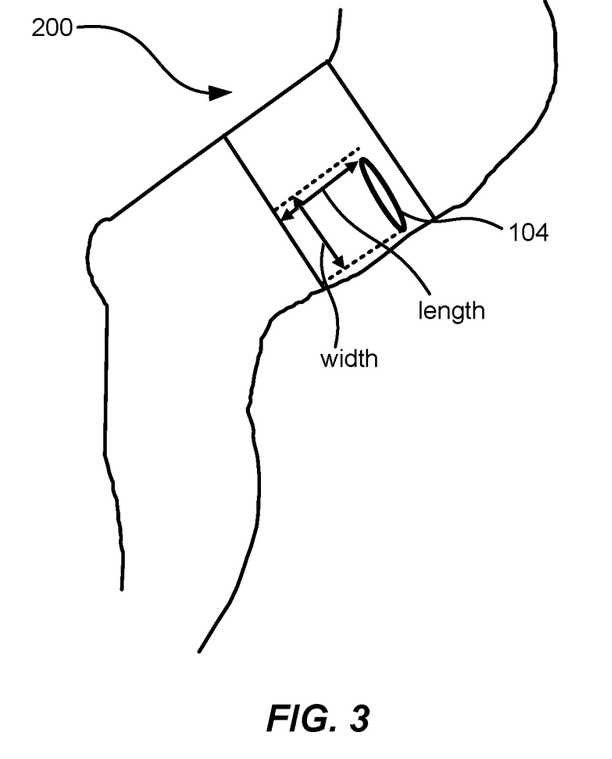
FIG. 3 is an illustration of another exemplary wearable accessory carrier in accordance with aspects of the invention.

With reference to the embodiments illustrated in FIGS. 2-3, a wearable accessory carrier 100 is provided that includes a belt 102 configured to carry or secure one or more peripheral components of system 10. The belt 102 may include one or more compartments 104 (e.g., pockets, pouches, holders) configured to receive, store, and retain the system controller 20, batteries 22, a portion of the driveline cable 25 (e.g., the external cable 27), other cables (e.g., cables connecting the batteries 22 to controller 20), or other peripheral components as described in more detail below. In some embodiments, the belt 102 may be sized to fit over (e.g., configured to be worn on) a patient's waist 30. In other embodiments, the belt 102 may be sized to fit over other portions (e.g., torso) or limbs of a patient. For example, the belt 102 may be sized to fit over an arm, calf, or thigh of a patient (see FIG. 3).

In some embodiments, the belt 102 is made of an elastic material such that the belt 102 may be slipped on and off a patient. The elasticity allows the belt 102 to fit snugly on the patient and have a low profile such that it may be worn over or under the patient's clothing. Additionally, the belt 102 may be adjusted or positioned higher or lower on a patient's body as desired by the patient (e.g., for comfortability) and in a substantially fixed position. Further, elasticity of the belt 102 may allow a single belt to fit a range of patient sizes which may reduce an amount of stock keeping units (e.g., SKUs) required. Also, elasticity of the belt 102 allows components of different sizes to be stored within the compartments 104 while maintaining a snug fit around the patient when worn. In some embodiments, the belt 102 may include a strip of non-slip material 106 (e.g., rubber, silicone) on an inner side of the belt to help prevent the belt 102 from substantially shifting positions on the patient when worn. In some embodiments, the belt 102 may have a different or additional closure or fastening mechanism (e.g., button, hook and loop, zipper, magnet, buckle) for maintaining the belt in position on a patient. While in other embodiments, elasticity of the belt 102 is sufficient to hold or maintain the belt in position on the patient without an additional closure mechanism, non-slip material, and/or other supporting component (e.g., shoulder straps or harnesses).

As discussed above, the belt 102 includes a plurality of integrated compartments 104 disposed around inner and outer circumferences of the belt 102. The integrated compartments 104 are configured to hold and retain one or more peripheral components of the system 10 therein. The compartments 104 are integrated within the belt 102 to maintain its low profile and also such that no additional securement devices are required to couple the compartments 104 to the belt 102. The compartments 104 are integrated into the belt 102 such that they are made of the same material as the belt 102 (e.g., an elastic material). Positioning multiple compartments 104 completely or substantially completely around the inner and outer circumferences of the belt 102 may provide improved modularity. A patient may independently adjust location or placement of the various peripheral components of system 10 within the compartments 104 as desired. For example, the patient may move or position the peripheral components within any of the compartments 104 to improve weight distribution, balance, or comfort. Depending on activity, the patient may move the peripheral components to different compartments 104 (e.g., to a left or right, front, or rear side of the belt 102) to reduce interference with the patient's activity. Additionally, a patient may place personal items (e.g., wallet, keys, sunglasses, mobile device, medication) in the compartments 104. Holding personal items in the compartments 104 on the inner circumference of the belt may better conceal such items from others.

Positioning multiple compartments 104 completely or substantially completely around the inner and outer circumferences of the belt 102 may also provide reversibility. Because compartments 104 are disposed on both inner and outer circumferences, the belt may be worn with either the inner or outer circumference compartments 104 facing outward relative to a patient when worn on the patient. This may provide improved convenience for the patient.

In some embodiments, the plurality of integrated compartments 104 may include openings 108 formed from slits or openings in the belt 102. Elasticity of the belt 102 may sufficiently close the openings 108 or maintain the peripheral components within the compartments 104. In other embodiments, additional or different fastening mechanisms may be used to close the compartments 104. For example, the compartments 104 may include hook and loop, zippers, buttons, magnets, or other suitable fastening mechanisms. In certain embodiments, the compartments 104 may further include flaps or additional material that covers or extends over the slits or openings 108 to provide further securement of components held within the compartments 104. These flaps may also include fasteners.

In some embodiments, the plurality of integrated compartments 104 may have a same or substantially equivalent size to maintain modularity or versatility. For example, the compartments 104 may be sized (e.g., have a length, width, and/or depth) such that a larger of the peripheral components (e.g., the controller 20 or battery 22) may fit within each compartment. As such, any of the peripheral components may be moved or positioned around the belt as desired (e.g., may fit into any of the compartments). For example, in some embodiments, the compartments 104 may have a length between about 2" to about 4", a width between about 3.5" to about 5.5", and/or a depth between about 0.5" to about 2". In some embodiments, the compartments 104 can be sized smaller than the controller 20 or battery 22 as the compartments 104 and belt 102 may be made of an elastic material. In some embodiments, the compartments 104 may be sized between + or − about 0.5" of a length, width, or depth dimension of the controller 20 or battery 22 depending on material elasticity. In some embodiments, the controller 20 is about 3.4" in length, about 5" in width, and about 1.18" in depth. The compartments 104 may be sized accordingly to fit a controller 20 with such dimensions.

Further, in some embodiments, the compartments 104 are sized such that a larger of the peripheral components may fit length-wise or width-wise in any of the compartments 104. Accordingly, the compartments 104 may be sized to be sufficiently long and wide such that any of the peripheral components may be positioned vertically, horizontally, or at an angle within such compartments. Further, as the controller 20 may have a user interface, each compartment 104 may have a window (e.g., transparent portion) such that the user interface or display is visible when held in the compartments 104. In other embodiments, the compartments 104 may be manufactured out of a wide weave mesh or other material such that the interface or display is visible through the compartments 104.

In yet further embodiments, the belt 102 may include other retention mechanisms (e.g., snap closures, hook and loop, buttons, magnets) positioned on an inner or outer circumference of the belt. For example, the belt 102 may include one or more snap closures 130. The snap closures 130 are configured to hold or retain cables (e.g., driveline cable, power cable, or other leads) in position on the belt or place near a patient's body. This helps prevent or reduce tugging on such cables, thereby reducing a risk of infection (e.g., as the driveline cable extends percutaneously through the exit site as discussed above) or disconnection.

As discussed above, the belt 102 may be made from an elastic material to provide an adjustable, but snug fit. In other embodiments, it may be desirable that the belt 102 also be washable, cool or sweat-wicking, water-proof, or quick to dry. In some embodiments, the belt 102 may be made from neoprene or another suitable material.

With reference to FIG. 3, a wearable accessory carrier 200 may be configured similarly or identical to the wearable accessory carrier 100 (e.g., including an elastic belt and integrated compartments 104). However, as discussed above, in some embodiments, the wearable accessory carrier 200 may be sized to fit on a patient's limb such as a leg (e.g., thigh, calf). For certain patients, this provides improved concealment of certain peripheral components under clothing such as a dress. In some embodiments, the accessory carrier 200 includes one or more compartments 104 configured to hold (e.g., having a length and width) only one of a controller 20 or battery 22. Such carriers 200 sized to fit around a patient's leg may be too small to carry both controller 20 and batteries 22.

Figure 4A:
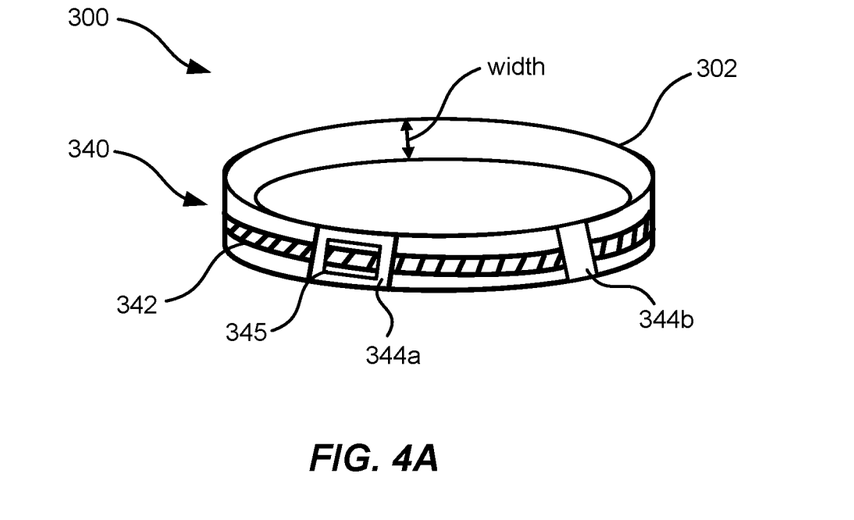
FIG. 4A is an illustration of another exemplary wearable accessory carrier in accordance with aspects of the invention.

FIG. 4A illustrates another wearable accessory carrier 300 that includes a belt 302 configured to carry or secure one or more peripheral components of system 10. The carrier 300 may include one or more of any of the features described above, in whole or in part, with respect to carriers 100 and 200. For example, the belt 302 may be made of an elastic material such that the belt 302 may be slipped on and off a patient. In other embodiments, the belt 302 may include other fastening mechanisms to allow the belt 302 to be secured on the patient. The belt 302 may be sized to fit over a patient's waist 30. In other embodiments, the belt 302 may be sized to fit over other portions (e.g., torso) or limbs (e.g., arms, legs, calf, thigh) of a patient.

The belt 302 includes a retention mechanism 340 such as a magnetic strip 342 or plurality of magnets. The magnetic strip 342 extends length-wise along or around the belt 302. The magnetic strip 342 can carry or secure a plurality of separate compartments 344 (e.g., pouches, pockets, holders) to the belt 302. While the magnetic strip 342 is illustrated as having a substantially uniform width, in other embodiments, the magnetic strip 342 may have a non-uniform width. For example, some portions or sections of the magnetic strip 342 may have an increased or larger width relative to other sections (e.g., sized such that the compartments 344 may be oriented or affixed to such larger width sections in vertical, horizontal, or stacked configurations as described in more detail below). In yet further embodiments, the magnetic strip 342 may extend around belt 302 in a non-continuous manner (e.g., having a plurality of discrete sections or portions spaced apart from each other).

The one or more compartments 344 (e.g., pockets, pouches, holders) may be configured to receive, store, and retain the system controller 20, batteries 22, a portion of the driveline cable 25 (e.g., the external cable 27), other cables (e.g., cables connecting the batteries 22 to controller 20), or other peripheral components. The compartments 344 include a corresponding magnet or magnetic strip 346 configured to attach to magnetic strip 342 such that compartments 344 may be detachably secured to belt 302. This provides modularity as a patient may affix individual compartments 344 to any desired location along magnetic strip 342. The patient may move (e.g., attach or detach) compartments 344 and therefore, location of the components to be received therein as desired along strip 342.

While the compartments 344 are illustrated in FIG. 4A as being oriented in a substantially horizontal configuration (e.g., with openings 308 facing superiorly) when affixed to the belt 302 and worn on the patient's waist 30, the compartments 344 may also be oriented or affixed to the belt 302 in a substantially vertical configuration (e.g., with openings 308 facing medially or laterally). The compartments 344 may also be oriented or affixed to the belt 302 at an oblique angle. This provides further modularity as the patient may affix individual compartments 344 horizontally, vertically, or at an oblique angle to the belt 302. In some embodiments, a width W of the belt 302 or strip 342 may be configured or sized such that the compartments 344 may be oriented or affixed to the belt 302 in a horizontal configuration, vertical configuration, or at an oblique angle. In further embodiments, the width W of the belt 302 or strip 342 may be configured or sized such that two or more of the compartments 344 (e.g., 2, 3, or 4) may be affixed to the belt 302 in a stacked configuration (e.g., horizontally or vertically). In yet further embodiments, the width W of the belt 302 or strip 342 may be configured or sized such that two or more of the compartments 344 may be affixed to the belt 302 in a stacked configuration such that at least one of the stacked compartments 344 is affixed in a horizontal configuration and at least one of the stacked compartments 344 is affixed in a vertical configuration.

As discussed above with respect to compartments 104, compartments 344 may have a same or substantially equivalent size. Compartments 344 may be sized (e.g., having a length and width) such that a larger of the peripheral components (e.g., of the controller 20 or battery 22) may fit within each compartment. In some embodiments, the compartments 344 are sized such that a larger of the peripheral components may fit length-wise or width-wise in any of the compartments 344. Accordingly, the compartments 344 may be sized to be sufficiently long and wide such that any of the peripheral components may be positioned vertically, horizontally, or at angle within such compartments. Each compartment 344 may have a window 345 (e.g., transparent portion) such that a user interface or display of the controller 20 is visible when held in the compartments 344. In other embodiments, the compartments 344 may be manufactured out of a wide weave mesh or other material such that the interface or display is visible through the compartments 344.

In other embodiments, the compartments 344 may have different sizes. A variety of different sized compartments 344 (e.g., identified individually as 344a and 344b) may be provided, sized to fit different components. For example, one compartment 344 may be sized to fit the controller 20 and a second compartment may be sized to fit the battery 22. In such embodiments, if the controller 20 is larger than the battery 22, the controller 20 may not fit within a compartment sized to only fit the battery 22. Similarly, if the battery 22 is larger than the controller 20, the battery 22 may not fit within a compartment sized to only fit the controller 20. The compartments 344 may be positioned or attached to the belt 302 at locations as desired for increased weight management, distribution, comfort, or reducing interference with a specific patient activity.

Figure 4B:
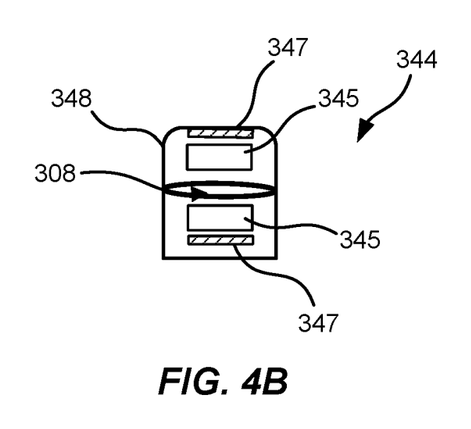
FIGS. 4B-4C are illustrations of front and back views of an exemplary modular compartment of the wearable accessory carrier of FIG. 4A in accordance with aspects of the invention.
Figure 4C:
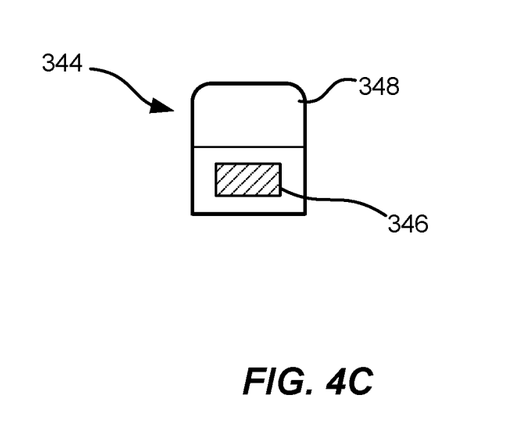

In some embodiments, the compartments 344 may also include fastening mechanisms used to close the compartments 344. For example, the compartments 104 may include flaps 348 or additional material that cover or extend over openings of the compartment 344 for receiving the peripheral components. The flaps 348 may be secured in a closed position with magnets 347 or other closure mechanisms (e.g., hook and loop, zippers, buttons, or other suitable fastening mechanisms) to retain the components within the compartment 344. The flaps 348 may be opened such that the components may be removed or adjusted as needed. In other embodiments, no flaps are included and the compartment openings may include the fastening mechanisms described above.

While the retention mechanism 340 is illustrated as a magnetic strip 342, in other embodiments, other types of retention mechanisms may be used to provide customizable attachment of compartments 344 to belt 302. For example, retention mechanism 340 and compartments 344 may include hook and loop fasteners to allow for detachably coupling the compartments 344 to various positions or locations along belt 302. In other embodiments, the retention mechanism 340 may include snap closures. Further, as described above with respect to carriers 100 and 200, the belt 302 may also include other retention mechanisms (e.g., snap closures, hook and loop, buttons, magnets) positioned on an inner or outer circumference of the belt configured to hold or retain cables (e.g., driveline cable, power cable, or other leads) in place near a patient's body.

In the description above, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The term "or" in reference to a list of two or more items, covers all of the following interpretations of the word: any of the items in the list, all of the items in the list, and any combination of items in the list. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A mechanical circulatory support system comprising:
   a ventricular assist device configured for implantation in a patient to pump blood from a ventricle of the patient to circulate the pumped blood in the patient's vascular system;
   a percutaneous driveline cable;
   a system controller operatively connected to the ventricular assist device via the percutaneous driveline cable, wherein the system controller is configured to supply power to the ventricular assist device through the percutaneous driveline cable and control operation of the ventricular assist device via the percutaneous driveline cable; and
   a wearable accessory carrier comprising an elastic belt, inner circumference integrated compartments, outer circumference integrated compartments, and inner circumference retention mechanisms, wherein the elastic belt is configured to be worn on a waist of the patient, wherein the inner circumference integrated compartments are disposed around an inner circumference of the elastic belt, wherein the outer circumference integrated compartments are disposed around an outer circumference of the elastic belt, wherein the system controller is carried in one of the inner circumference integrated compartments or one of the outer circumference integrated compartments, wherein the inner circumference retention mechanisms are positioned on the inner circumference of the elastic belt at two or more points along the inner circumference of the elastic belt, and wherein the inner circumference retention mechanisms conform a portion of the percutaneous driveline cable to the inner circumference of the elastic belt.

2. The mechanical circulatory support system of claim 1, wherein the wearable accessory carrier is reversible such that either the inner circumference integrated compartments or the outer circumference integrated compartments may face outward away from the patient when the wearable accessory carrier is worn by the patient.

3. The mechanical circulatory support system of claim 1, wherein the wearable accessory carrier comprises a non-slip material disposed on the inner circumference of the elastic belt.

4. The mechanical circulatory support system of claim 1, wherein the elastic belt is made of neoprene.

5. The mechanical circulatory support system of claim 1, wherein the inner circumference integrated compartments and the outer circumference integrated compartments have substantially equivalent sizes.

6. The mechanical circulatory support system of claim 1, wherein the inner circumference integrated compartments and the outer circumference integrated compartments are sized such that the system controller may be positioned vertically and horizontally within each of the inner circumference integrated compartments and the outer circumference integrated compartments.

7. The mechanical circulatory support system of claim 1, further comprising a battery that provides electrical power to power operation of the ventricular assist device during battery powered operation of the ventricular assist device, wherein the battery is carried in one of the inner circumference integrated compartments or one of the outer circumference integrated compartments.

8. The mechanical circulatory support system of claim 1, wherein the inner circumference integrated compartments and the outer circumference integrated compartments are accessible via slit openings in the elastic belt.

9. The mechanical circulatory support system of claim 8, wherein the slit openings comprise flaps configured to cover the openings.

10. The mechanical circulatory support system of claim 8, wherein the inner circumference integrated compartments and the outer circumference integrated compartments comprise fasteners.

11. The mechanical circulatory support system of claim 1, wherein the system controller comprises a display and is carried in one of the outer circumference integrated compartments that comprises a window through which the display is visible.

12. The mechanical circulatory support system of claim 1, wherein the system controller comprises a display and is carried in one of the outer circumference integrated compartments that is formed from a material through which the display is visible.

13. The mechanical circulatory support system of claim 1, wherein the elastic belt comprises a fastener configured to secure the elastic belt on the patient.

14. The mechanical circulatory support system of claim 1, wherein the inner circumference retention mechanisms comprise at least one of snap closures, hook and loop fasteners, buttons, or magnets.

15. A mechanical circulatory support system comprising:
a ventricular assist device configured for implantation in a patient to pump blood from a ventricle of the patient to circulate the pumped blood in the patient's vascular system;
a percutaneous driveline cable;
a system controller operatively connected to the ventricular assist device via the percutaneous driveline cable, wherein the system controller is configured to supply power to the ventricular assist device through the percutaneous driveline cable and control operation of the ventricular assist device via the percutaneous driveline cable; and
a wearable accessory carrier comprising a belt, a magnetic strip, a first storage compartment, and inner circumference retention mechanisms, wherein the belt is configured to be worn on a waist of the patient, wherein the magnetic strip extends lengthwise along the belt, wherein the first storage compartment carries the system controller, wherein the first storage compartment includes a magnet via which the first storage compartment is detachably couplable to multiple positions on the magnetic strip of the belt, wherein the inner circumference retention mechanisms are positioned on an inner circumference of the belt at two or more points along the inner circumference of the belt, and wherein the inner circumference retention mechanisms conform a portion of the percutaneous driveline cable to the inner circumference of the belt.

16. The mechanical circulatory support system of claim 15, wherein the belt is made of an elastic material.

17. The mechanical circulatory support system of claim 15, wherein the first storage compartment comprises a flap cover configured to be secured over an opening of the first storage compartment.

18. The mechanical circulatory support system of claim 15, further comprising a battery, wherein the battery is configured to supply electrical power to power operation of the ventricular assist device during battery powered operation of the ventricular assist device, wherein the wearable accessory carrier comprises a second storage compartment, wherein the battery is carried in the second storage compartment.

19. A mechanical circulatory support system comprising:
a ventricular assist device configured for implantation in a patient to pump blood from a ventricle of the patient to circulate the pumped blood in the patient's vascular system;
a percutaneous driveline cable;
a system controller operatively connected to the ventricular assist device via the percutaneous driveline cable, wherein the system controller is configured to supply power to the ventricular assist device and control operation of the ventricular assist device; and
a wearable accessory carrier comprising a belt, a hook and loop strip, a first storage compartment, and inner circumference retention mechanisms, wherein the belt is configured to be worn on a waist of the patient, wherein the hook and loop strip extends lengthwise along the belt, wherein the first storage compartment carries the system controller, wherein the first storage compartment includes a hook and loop fastener such that the first storage compartment is detachably couplable to multiple positions on the hook and loop strip of the belt, wherein the inner circumference retention mechanisms are positioned on the inner circumference of the belt at two or more points along the inner circumference of the belt, and wherein the inner circumference retention mechanisms conform a portion of the percutaneous driveline cable to the inner circumference of the belt.

20. The mechanical circulatory support system of claim 19, wherein the belt is made of an elastic material.

21. The mechanical circulatory support system of claim 19, wherein the first storage compartment comprises a flap cover configured to be secured over an opening of the first storage compartment.

22. The mechanical circulatory support system of claim 19, further comprising a battery, wherein the battery is configured to supply electrical power to power operation of the ventricular assist device during battery powered operation of the ventricular assist device, wherein the wearable accessory carrier comprises a second storage compartment, wherein the battery is carried in the second storage compartment.

23. The mechanical circulatory support system of claim 19, wherein the system controller comprises a display and the first storage compartment comprises a window through which the display is visible.

24. The mechanical circulatory support system of claim 23, wherein the inner circumference retention mechanisms comprise at least one of snap closures, hook and loop fasteners, buttons, or magnets.

* * * * *